United States Patent

Buchecker et al.

[11] Patent Number: 5,328,637
[45] Date of Patent: Jul. 12, 1994

[54] ALKINYL-DERIVATIVES AND THEIR USE IN LIQUID CRYSTALLINE MIXTURES

[75] Inventors: Richard Buchecker, Zurich; Martin Schadt, Seltisberg, both of Switzerland

[73] Assignee: Hoffmann-La Roche Inc., Nutley, N.J.

[21] Appl. No.: 837,512

[22] Filed: Feb. 18, 1992

[30] Foreign Application Priority Data

Feb. 25, 1991 [CH] Switzerland .................. 557/91

[51] Int. Cl.$^5$ .................. C09K 19/06; C09K 19/34; C09K 19/30; G02G 1/13
[52] U.S. Cl. .................. 252/299.60; 252/299.61; 252/299.63; 252/299.66; 549/369; 549/370; 544/298; 546/339
[58] Field of Search .......... 252/299.01, 299.6, 299.66, 252/299.61, 299.63; 549/369, 370; 544/298; 546/339

[56] References Cited

U.S. PATENT DOCUMENTS

| | | | |
|---|---|---|---|
| 4,528,114 | 7/1985 | Petrzilka et al. | 252/299.6 |
| 5,171,473 | 12/1992 | Buchecker et al. | 252/299.61 |
| 5,264,149 | 11/1993 | Buchecker et al. | 252/299.6 |

FOREIGN PATENT DOCUMENTS

| | | |
|---|---|---|
| 409634 | 1/1991 | European Pat. Off. |
| 427957 | 7/1991 | European Pat. Off. |
| 3734517 | 10/1987 | Fed. Rep. of Germany |
| 3906019 | 2/1989 | Fed. Rep. of Germany |
| 61/263935 | 7/1987 | Japan |
| 2111992 | 7/1983 | United Kingdom |

OTHER PUBLICATIONS

Petrzilka, Mol. Cryst. Liq. Cryst. 111:329–346 (1984).
Petrzilka, Mol. Cryst. Liq. Cryst. 111:347–358 (1984).
Abstract No. E14 L03 U11 V07.
Abstract No. E15 L03 U11 V07.

*Primary Examiner*—Robert L. Stoll
*Assistant Examiner*—C. Harris
*Attorney, Agent, or Firm*—George M. Gould; George W. Johnston; Robert A. Silverman

[57] ABSTRACT

Compounds of the formula

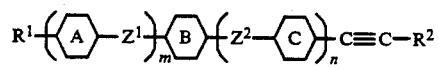

and liquid crystalline mixtures containing same.

14 Claims, No Drawings

ALKINYL-DERIVATIVES AND THEIR USE IN LIQUID CRYSTALLINE MIXTURES

FIELD OF THE INVENTION

The present invention is concerned with novel compounds having a terminal 1-alkynyl group, their manufacture, liquid crystalline mixtures which contain these compounds and the use of these compounds or mixtures for electro-optical purposes.

BACKGROUND OF THE INVENTION

Liquid crystals are used primarily as dielectrics in indicating devices, since the optical properties of such substances can be influenced by an applied voltage. Electro-optical devices based on liquid crystals are well-known to a person skilled in the art and can be based on various effects. Such devices are, for example, cells having dynamic scattering, DAP cells (deformation of aligned phases), guest/host cells, TN cells having a twisted nematic structure, STN cells ("super-twisted nematic"), SBE cells ("super-birefringence effect") and OMI cells ("optical mode interference"). The most common indicating devices are based on the Schadt-Helfrich effect and have a twisted nematic structure.

The liquid crystal materials must have a good chemical, photochemical and thermal stability and a good stability towards electric fields. Further, they should have a suitable mesophase over a broadest possible range (for example, a nematic or a cholesteric phase for the cells mentioned above), but nevertheless should have a sufficiently low viscosity and in the cells should permit short response times, low threshold potentials and a high contrast. Further properties such as the electrical conductivity, the dielectric anisotropy and the optical anisotropy must fulfil different requirements depending on the field of application and type of cell. For example, materials for cells having a twisted nematic structure should have a positive dielectric anisotropy and an electrical conductivity which is as low as possible. For DAP cells components having a negative dielectric anisotropy are necessary.

In order to fulfil these to some extent contradictory requirements mixtures with up to about 15 components must generally be produced. It is therefore important that the components have a good miscibility with one another and have a sufficient solubility.

In order to achieve a suffiently broad mesophase range there must be added to the mixtures mainly clearing point-increasing components which, however, can disadvantageously influence the viscosity and the electro-optical properties. Further, materials having a low optical anisotropy, which are of interest e.g. for actively addressed liquid crystal indicators, frequently give smectic tendencies and lead for the most part to an increase in the threshold potential and/or the response times. Furthermore, non-polar materials with high optical anisotropy often have only smectic mesophases or even no liquid crystalline properties.

SUMMARY OF THE INVENTION

The invention provides compounds of the general formula

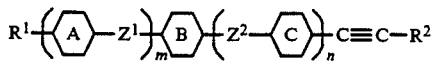

wherein
rings A and C each individually can be trans-1,4-cyclohexylene, 1,4-phenylene, trans-1,3-dioxane-2,5-diyl, pyridine-2,5-diyl or pyrimidine-2,5-diyl, with the proviso that not more than one of rings A and C can be pyridine-2,5-diyl or pyrimidine-2,5-diyl.
ring B is monofluoro-substituted or 2,3-difluoro-substituted 1,4-phenylene,
$Z^1$ or $Z^2$ signifies a single covalent bond and $Z^2$ or $Z^1$, respectively, signifies a single covalent bond, ethylene, oxymethylene or methyleneoxy,
m and n each independently signify 0, 1 or 2, whereby the sum m+n is 1 or 2,
$R^1$ signifies $C_{1-10}$-alkyl, $C_{2-9}$-alkoxyalkyl or $C_{1-9}$-alkoxy and
$R^2$ signifies $C_{1-10}$-alkyl,
with the proviso that two 1,4-phenylene rings are linked with each other only by a single bond.

The compounds in accordance with the invention are non-polar compounds having comparatively very broad mesophase ranges, high clearing points and pronounced nematic tendencies. In spite of the high clearing points they have an amazingly low viscosity and favourable electro-optical properties, in particular they permit short switching times, low threshold potentials and, depending on the selection of $R^1$, a modification of the elastic properties. Further, the optical anisotropy can be varied in a broad range; for example, the compounds of formula I in which rings A and C signify trans-1,4-cyclohexylene and/or trans-1,3-dioxane-2,5-diyl have low optical anisotropies and the compounds of formula I in which rings A and C signify 1,4-phenylene have particularly high optical anisotropies.

Having regard to the remarkable properties, the compounds in accordance with the invention also offer the possibility of reducing the number of components in the mixture and thereby of simplifying the mixture substantially. In this case it is of advantage that the compounds in accordance with the invention have a good miscibility with known materials and, having regard to the low melting enthalpies, also have good solubility in high concentrations.

It has been established that the compounds in accordance with the invention are very advantageously suited for DAP applications, but can also be used for STN applications.

DETAILED DESCRIPTION OF THE INVENTION

In Formula I above and in the above definition of the compounds I, the term monofluoro-substituted 1,4-phenylene for ring B embraces 2-fluoro-1,4-phenylene and 3-fluoro-1,4-phenylene. Under "$C_{1-10}$-alkyl", "$C_{2-9}$-alkoxyalkyl" and "$C_{1-9}$-alkoxy" for $R^1$ and/or $R^2$ there are to be understood not only straight-chain, but also branched groups.

Not only the position of the nitrogen atom or of the nitrogen atoms in the pyridine-2,5-diyl ring and, respectively, pyrimidine-2,5-diyl ring (ring A or C), but also the position of the oxygen atoms of the trans-1,3-dioxane-2,5-diyl ring (ring A and/or ring C) is directed only in the direction of the triple bond —C≡C—, i.e. such a ring when present is arranged as follows in formula I above:

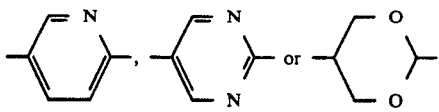

When $Z^1$ or $Z^2$ signifies oxymethylene (OCH$_2$) or methyleneoxy (CH$_2$O) this is preferably methyleneoxy.

Ring A is preferably trans-1,4-cyclohexylene, 1,4-phenylene or 1,3-dioxane-2,5-diyl, especially the first- or second-named group, which also applies independently to ring C. Ring B is, in turn, preferably 2,3-difluoro-1,4-phenylene. Preferably, $Z^1$ and $Z^2$ each independently signify a single bond or one of the groups $Z^1$ and $Z^2$ also ethylene. $R^1$ as alkyl, alkoxyalkyl or alkoxy preferably contains from 3 to 5 carbon atoms, while $R^2$ as alkyl is preferably $C_{1-3}$-alkyl.

Formula I preferably embraces the compounds of the following general formulae:

Ia 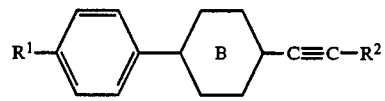

Ib 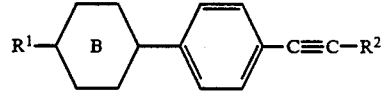

Ic 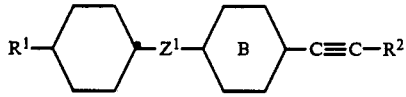

Id 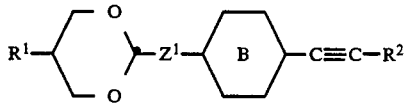

Ie 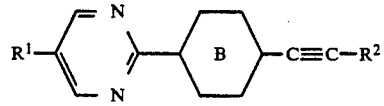

If 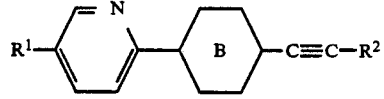

Ig 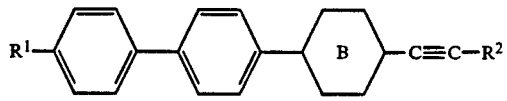

Ih 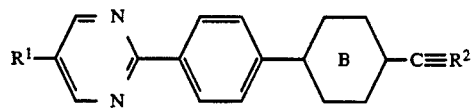

Ii 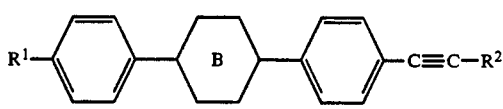

Ij 

Ik 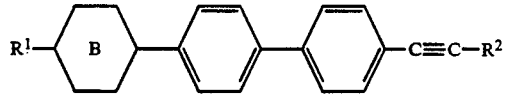

Il 

Im 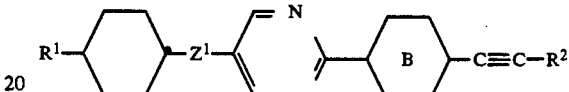

In 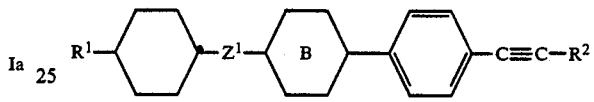

Io 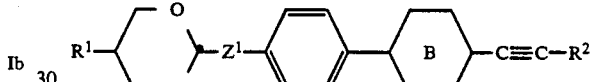

Ip 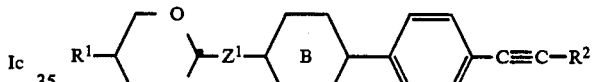

Iq 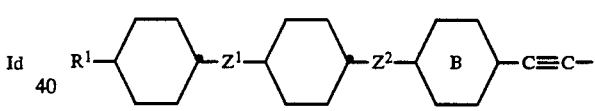

Individual representatives of the compounds of formula I are:

1-[4-(4-Propylphenyl)-phenyl]-2,3-difluoro-4-(1-propynyl)-benzene,

1-[4-(4-butylphenyl)-phenyl]-2,3-difluoro-4-(1-propynyl)-benzene,

1-[4-(4-hexylphenyl)-phenyl]-2,3-difluoro-4-(1-propynyl)-benzene,

1-[4-(4-ethylphenyl)-phenyl]-2,3-difluoro-4-(1-propynyl)-benzene,

1-[4-(4-propylphenyl)-phenyl]-2,3-difluoro-4-(1-butynyl)-benzene,

1-[4-(4-propylphenyl)-phenyl]-2,3-difluoro-4-(1-pentynyl)-benzene,

1-[4-(4-propylphenyl)-phenyl]-2-fluoro-4-(1-propynyl)-benzene,

1-[4-(4-propylphenyl)-phenyl]-3-fluoro-4-(1-propynyl)-benzene,

1-[4-(5-propyl-pyrimidin-2-yl)-phenyl-2,3-difluoro-4-(1-propynyl)-benzene,

1-[4-(5-pentyl-pyrimidin-2-yl)-phenyl-2,3-difluoro-4-(1-propynyl)-benzene,

1-[4-(5-propyl-pyridin-2-yl)-phenyl-2,3-difluoro-4-(1-propynyl)-benzene,

1-[4-(5-pentyl-pyridin-2-yl)-phenyl-2,3-difluoro-4-(1-propynyl)-benzene,

1-[4-(4-trans-propyl-cyclohexyl)-phenyl]-2,3-difluoro-4-(1-propynyl)-benzene,
1-[4-(4-trans-pentyl-cyclohexyl)-phenyl]-2,3-difluoro-4-(1-propynyl)-benzene,
1-[4-(4-trans-propyl-cyclohexyl)-phenyl]-2-fluoro-4-(1-propynyl)-benzene,
1-[4-(4-trans-propyl-cyclohexyl)-phenyl]-3-fluoro-4-(1-propynyl)-benzene,
1-[4-(5-trans-propyl-1,3-dioxan-2-yl)-phenyl]-3-fluoro-4-(1-propynyl)-benzene,
1-[4-trans-(4-trans-pentyl-cyclohexyl]-2,3-fluoro-4-(1-propynyl)-benzene,
1-{4-[2-(4-trans-propyl-cyclohexyl)-ethyl]-phenyl}-2,3-difluoro-4-(1-propynyl)-benzene,
1-{4-[2-(4-trans-propyl-cyclohexyl)-ethyl]-phenyl}-2-fluoro-4-(1-propynyl)-benzene,
1-{4-[2-(4-trans-propyl-cyclohexyl)-ethyl]-phenyl}-3-fluoro-4-(1-propynyl)-benzene,
1-{4-trans-[2-(4-trans-propyl-cyclohexyl)-ethyl]-cyclohexyl}-2,3-difluoro-4-(1-propynyl)-benzene,
1-{2-[4-trans-(4-trans-propyl-cyclohexyl)-cyclohexyl]-ethyl}-2,3-difluoro-4-(1-propynyl)-benzene,
1-{2-[4-trans-(4-trans-propyl-cyclohexyl)-cyclohexyl]-ethyl}-2-fluoro-4-(1-propynyl)-benzene,
1-{2-[4-(4-trans-propyl-cyclohexyl)-cyclohexyl]-ethyl}-3-fluoro-4-(1-propynyl)-benzene,
1-(4-propylphenyl)-2,3-difluoro-4-(1-propynyl)-benzene,
1-(4-pentylphenyl)-2-fluoro-4-(1-propynyl)-benzene,
1-(4-trans-propyl-cyclohexyl)-2,3-difluoro-4-(1-propynyl)-benzene,
1-(4-trans-pentyl-cyclohexyl)-2,3-difluoro-4-(1-propynyl)-benzene,
1-[2-(4-trans-propyl-cyclohexyl)-ethyl]-2,3-difluoro-4-(1-propynyl)-benzene,
1-(4-ethylphenyl)-2,3-difluoro-4-[4-(1-propynyl)-phenyl]-benzene,
1-(4-propylphenyl)-2,3-difluoro-4-[4-(1-propynyl)-phenyl]-benzene,
1(4-butylphenyl)-2,3-difluoro-4-[4-(1-propynyl)-phenyl]-benzene,
1-(4-hexylphenyl)-2,3-difluoro-4-[4(1-propynyl)-phenyl]-benzene,
1-(4-propylphenyl)-2,3-difluoro-4-[4-(1-butynyl)-phenyl]-benzene,
1-(4-propylphenyl)-2,3-difluoro-4-[4-(1-pentynyl)-phenyl]-benzene,
1-(4-propylphenyl)-2,3-difluoro-4-[4-(1-hexynyl)-phenyl]-benzene,
1-(4-propylphenyl)-2,3-difluoro-4-[4-(1-heptynyl)-phenyl]-benzene,
1-(4-propylphenyl)-2-fluoro-4-[4-(1-propynyl)-phenyl]-benzene,
1-(4-propylphenyl)-2-fluoro-4-[4-(1-propynyl)-phenyl]-benzene,
1-(4-pentylphenyl)-2-fluoro-4-[4-(1-propynyl)-phenyl]-benzene,
1-(4-pentylphenyl)-3-fluoro-4-[4-(1-propynyl)-phenyl]-benzene,
1-(4-trans-propyl-cyclohexyl)-2,3-difluoro-4-[4-(1-propynyl)-phenyl]-benzene,
1-(4-trans-pentyl-cyclohexyl)-2,3-difluoro-4-[4-(1-propynyl)-phenyl]-benzene,
1-[2-(4-trans-propyl-cyclohexyl)-ethyl]-2,3-difluoro-[4-(1-propynyl)-phenyl]-benzene,
1-(5-propyl-pyrimidin-2-yl)-2,3-difluoro-[4-(1-propynyl)-phenyl]-benzene,
1-(5-pentyl-pyrimidin-2-yl)-2,3-difluoro-[4-(1-propynyl)-phenyl]-benzene,
1-{4-[4-(1-propynyl)-phenyl]-phenyl}-2,3-difluoro-4-propyl-benzene,
1-{4-[4-(1-propynyl)-phenyl]-phenyl}-2,3-difluoro-4-butyl-benzene,
1-{4-[4-(1-propynyl)-phenyl]-phenyl}-2,3-difluoro-4-hexyl-benzene,
1-{4-[4-(1-propynyl)-phenyl]-phenyl}-2-fluoro-4-propyl-benzene,
1-{4-[4-(1-propynyl)-phenyl]-phenyl}-2-fluoro-4-butyl-benzene,
1-{4-[4-(1-propynyl)-phenyl]-phenyl}-2-fluoro-4-pentyl-benzene,
1-{4-[4-(1-propynyl)-phenyl]-phenyl}-3-fluoro-4-propyl-benzene,
1-{4-[4-(1-propynyl)-phenyl]-phenyl}-3-fluoro-4-butyl-benzene,
1-{4-[4-(1-propynyl)-phenyl]-phenyl}-3-fluoro-4-pentyl-benzene,
1-{4-[4-(1-butynyl)-phenyl]-phenyl}-2,3-difluoro-4-propyl-benzene,
1-{4-[4-(1-pentenyl)-phenyl]-phenyl}-2,3-difluoro-4-propyl-benzene,
1-{4-[4-(1-butynyl)-phenyl]-phenyl}-2-fluoro-4-propyl-benzene,
1-{4-[4-(1-butynyl)-phenyl]-phenyl}-3-fluoro-4-propyl-benzene,
1-{4-[4-trans-(1-propynyl)-cyclohexyl]-phenyl}-2,3-difluoro-4-propyl-benzene,
1-{4-[4-trans-(1-propynyl)-cyclohexyl]-phenyl}-2,3-difluoro-4-pentyl-benzene,
1-{4-[4-trans-(1-propynyl)-cyclohexyl]-phenyl}-2-fluoro-4-pentyl-benzene,
1-{4-[4-trans-(1-propynyl)-cyclohexyl]-phenyl}-3-fluoro-4-pentyl-benzene,
1-[4-{2-[4-trans-(1-propynyl)-cyclohexyl]-ethyl}-phenyl]-2,3-difluoro-4-propyl-benzene,
1-[4-{2-[4-trans-(1-propynyl)-cyclohexyl]-ethyl}-phenyl]-2-fluoro-4-propyl-benzene,
1-[4-{2-[4-trans-(1-propynyl)-cyclohexyl]-ethyl}-phenyl]-3-fluoro-4-propyl-benzene,
1-{4-trans-[4-trans-(1-propynyl)-cyclohexyl]-cyclohexyl}-2,3-difluoro-4-propyl-benzene,
1-[4-trans-{2-[4-trans-(1-propynyl)-cyclohexyl]-ethyl}-cyclohexyl]-2,3-difluoro-4-propyl-benzene,
1-[4-(1-propynyl)-phenyl]-2,3-difluoro-4-propyl-benzene,
1-[4-(1-pentynyl)-phenyl]-2,3-difluoro-4-propyl-benzene,
1-}4-[5-(1-propynyl)-pyrimidin-2-yl]-phenyl}-2,3-difluoro-4-propyl-benzene,
1-{4-[5-(1-propynyl)-pyrimidin-2-yl]-phenyl}-2-fluoro-4-propyl-benzene,
1-{4-[5-(1-propynyl)-pyrimidin-2-yl]-phenyl}-3-fluoro-4-propyl-benzene,
1-{4-[5-(1-propynyl)-pyridin-2-yl]-phenyl}-2,3-difluoro-4-propyl-benzene,
1-{4-[5-(1-propynyl)-pyridin-2-yl]-phenyl}-2-fluoro-4-propyl-benzene,
1-{4-[5-(1-propynyl)-pyridin-2-yl]-phenyl}-3-fluoro-4-propyl-benzene,
1-{5-[4-(1-propynyl)-phenyl]-pyridin-2-yl}-2,3-difluoro-4-propyl-benzene.

The compounds of formula I can be manufactured according to methods known per se, e.g. in accordance with the following Reaction Schemes 1 and 2. The respective intermediates and, respectively, starting materials are known or can be produced according to methods known per se. The methods which are used and which are presented in these Reaction Schemes are described extensively in the technical literature and are familiar to any person skilled in the art.
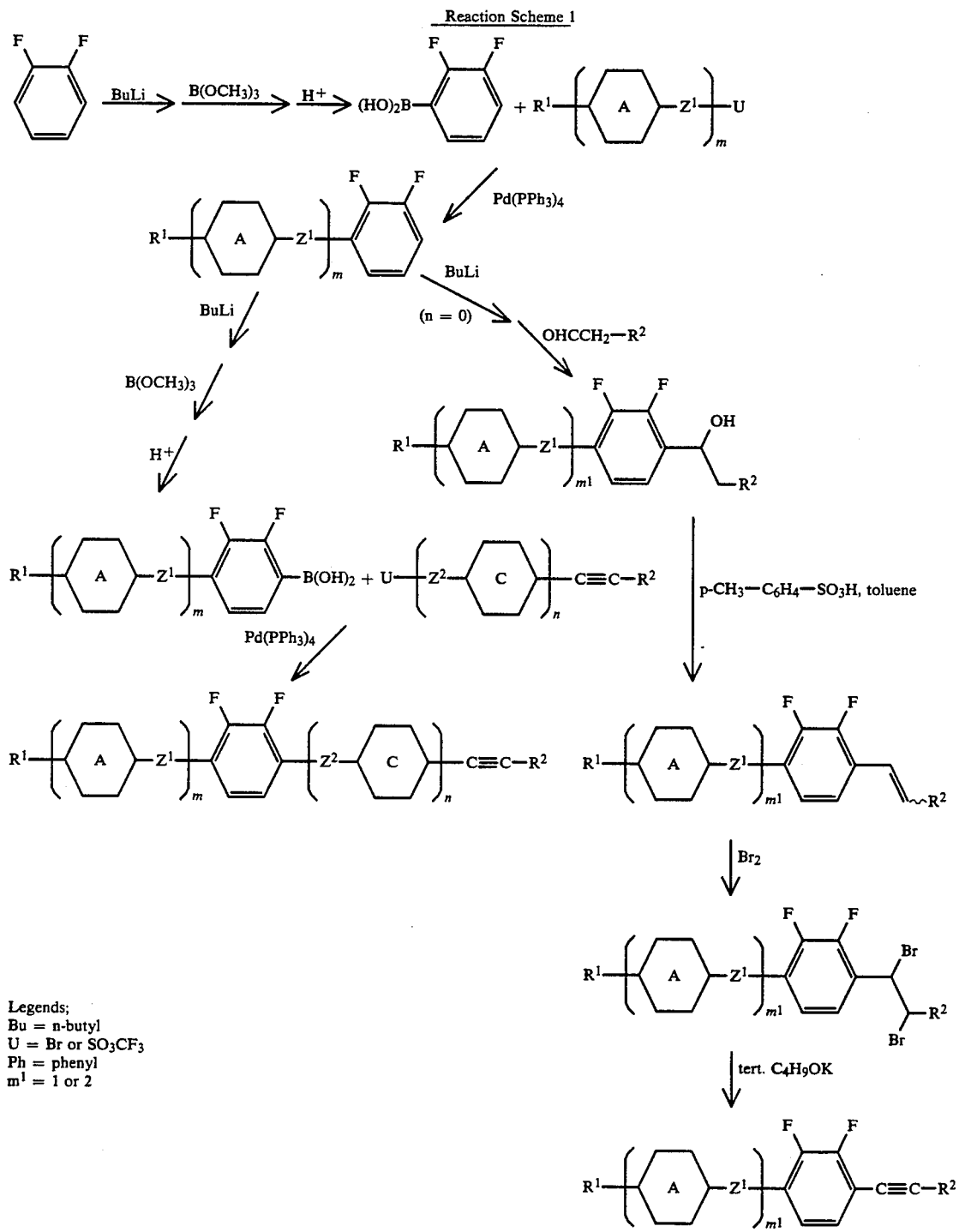
Legends;
Bu = n-butyl
U = Br or SO$_3$CF$_3$
Ph = phenyl
m$^1$ = 1 or 2

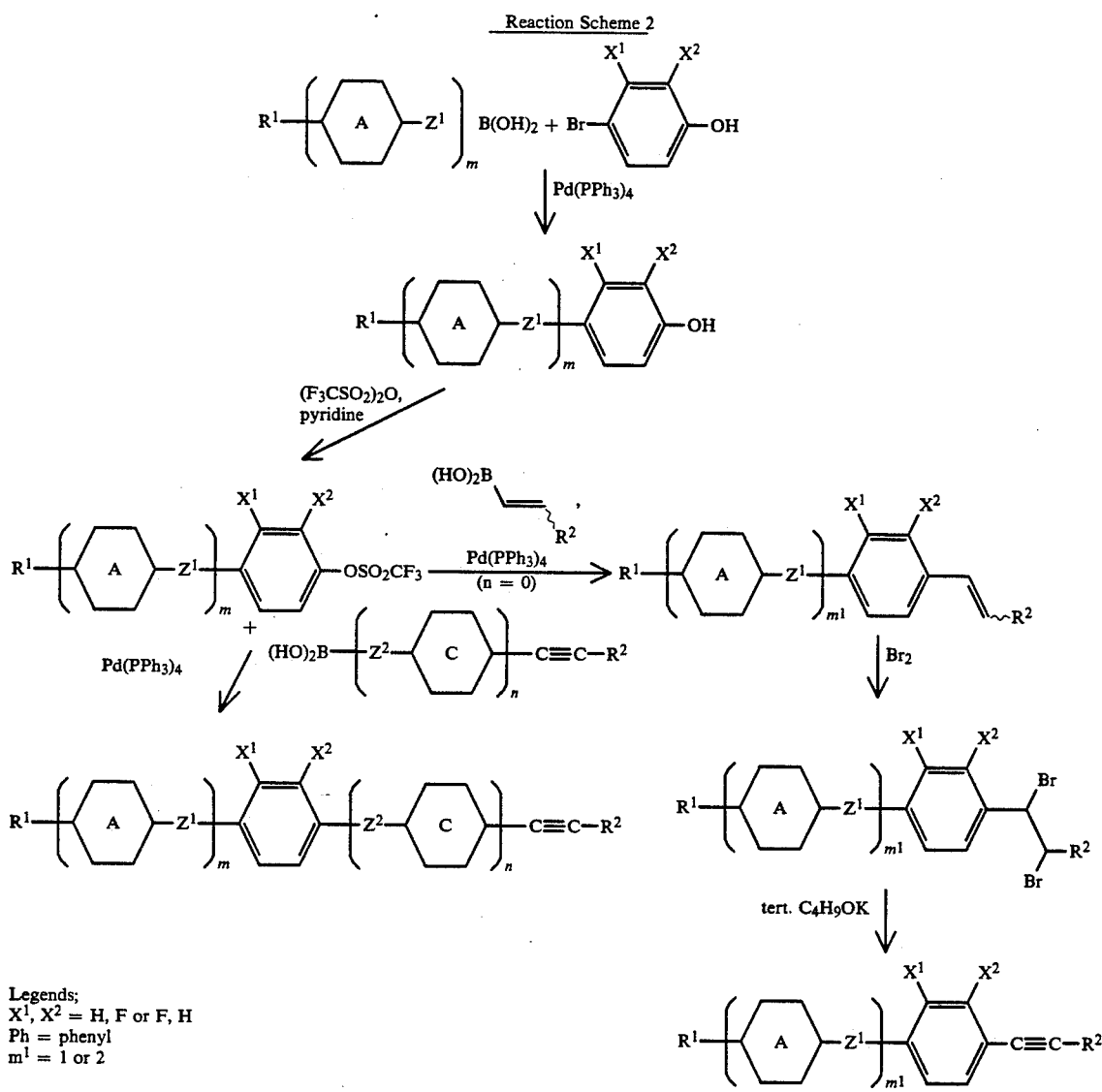

Legends;
$X^1, X^2 =$ H, F or F, H
Ph = phenyl
$m^1 =$ 1 or 2

The compounds of formula I can be used in the form of mixtures with one another and/or with other liquid crystal components such as e.g. with substances from the classes of azobenzenes, azoxybenzenes, phenylbenzoates, cyclohexanecarboxylic acid phenyl esters, cyclohexanecarboxylic acid cyclohexyl esters, biphenyls, phenylcyclohexanes, cyclohexylcyclohexanes, phenylpyrimidines, cyclohexylpyrimidines, phenyldioxanes, 2-cyclohexyl-1-phenylethanes, terphenyls, cyclohexylbiphenyls, phenylbicyclohexanes and cyclohexylphenylpyrimidines. Such substances are known to a person skilled in the art and, moreover, many of them are commercially available.

The liquid crystalline mixtures in accordance with the invention contain at least two components, of which at least one component is a compound of formula I. A second component and optionally additional components can be further compounds of formula I and/or other liquid crystal components.

The compounds of formula I are suitable especially for nematic mixtures or, insofar as at least one component of the mixture is optically active, also for cholesteric mixtures. A preferred field of application relates to use as dielectrics in liquid crystal indicating devices having a twisted nematic liquid crystal structure such as TN cells, STN cells, SBE cells, DAP cells, guest/host cells and OMI cells. Preferred mixtures are therefore those which contain one or more compounds of formula I and one or more compounds having a positive and/or negative dielectric anisotropy.

Having regard to the good solubility of the compounds of formula I in other liquid crystal materials and having regard to their good miscibility with one another, the content of compounds of formula I in the mixtures in accordance with the invention can be relatively high. In general, a content of about 2-50 wt. %, especially about 3-30 wt. %, of compounds of formula I is preferred.

The mixtures in accordance with the invention preferably contain, in addition to one or more compounds of formula I, one or more compounds from the group of compounds of the general formulae

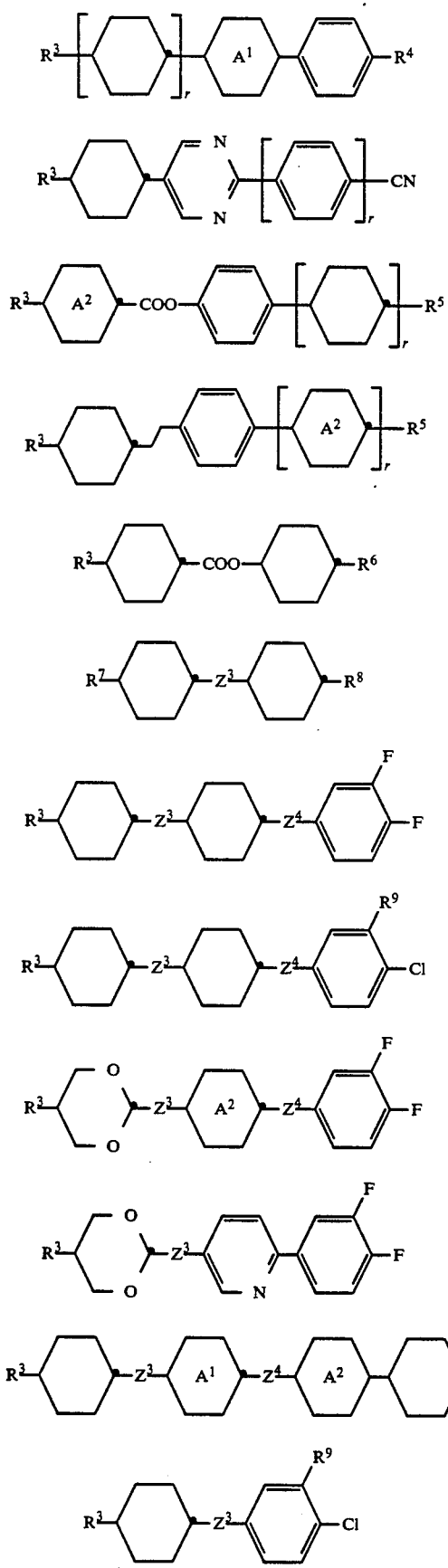
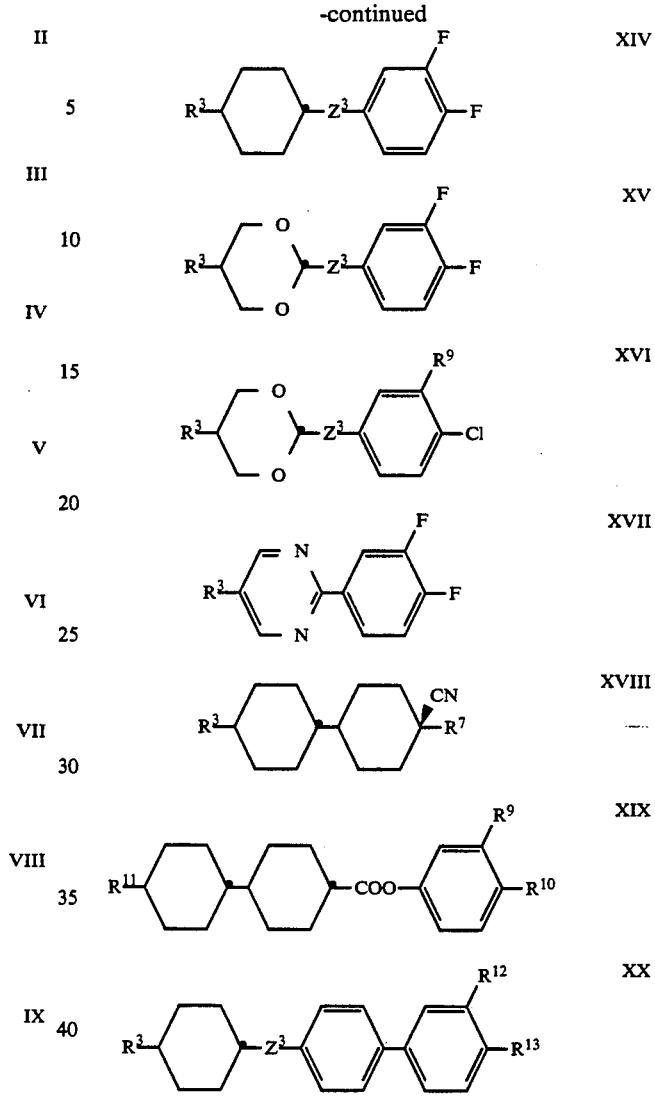

wherein r stands for the number 0 or 1; $R^3$ and $R^6$ each independently signify alkyl, alkoxyalkyl, 3E-alkenyl, 4-alkenyl or on a saturated ring also 1E-alkenyl; ring $A^1$ represents 1,4-phenylene, trans-1,4-cyclohexylene, pyridine-2,5-diyl, pyrimidine-2,5-diyl or trans-1,3-dioxane, -2,5-diyl; $R^4$ denotes cyano, isothiocyanato, fluorine, alkyl, 3E-alkenyl, 4-alkenyl, alkoxy, 2E-alkenyloxy, 3-alkenyloxy, difluoromethoxy, trifluoromethoxy or 1-alkynyl; ring $A^2$ represents 1,4-phenylene or trans-1,4-cyclohexylene; $R^5$ signifies alkyl, 3E-alkenyl, 4-alkenyl or on a cyclohexane ring also 1E-alkenyl or on a benzene ring also cyano, isothiocyanato, alkoxy, 2E-alkenyloxy or 3-alkenyloxy; $R^7$ denotes alkyl, 1E-alkenyl, 3E-alkenyl or 4-alkenyl; $Z^3$ and $Z^4$ each represent a single bond or ethylene, whereby two aromatic rings are linked only by a single bond; $R^8$ signifies cyano, alkyl, 1E-alkenyl, 3E-alkenyl, 4-alkenyl, alkoxy, 2E-alkenyloxy, 3-alkenyloxy, alkoxymethyl or (2E-alkenyl-)oxymethyl; $R^9$ denotes hydrogen, fluorine or chlorine; $R^{10}$ signifies fluorine, chlorine, difluoromethoxy, trifluoromethoxy or cyano; $R^{11}$ represents alkyl, 1E-alkenyl, 3E-alkenyl or 4-alkenyl; $R^{12}$ signifies hydrogen or fluorine; and $R^{13}$ denotes fluorine, chlorine, difluoromethoxy or trifluoromethoxy.

The above term "saturated ring" embraces trans-1,4-cyclohexylene and trans-1,3-dioxane-2,5-diyl. Residues $R^3$ to $R^8$ and $R^{11}$ each preferably have a maximum of 12 carbon atoms, particularly a maximum of 7 carbon atoms. Straight-chain residues are generally preferred.

The manufacture of the liquid crystalline mixtures and of the electro-optical devices can be effected in a manner known per se.

The invention is illustrated in more detail by the following Examples. In Examples 1-3 cl.p. signifies clearing point, C signifies a crystalline phase, $S_B$ signifies a smectic B phase, N signifies a nematic phase and I signifies the isotropic phase.

The following Examples illustrate the present invention but are not intended to limit its extent in any manner. While the examples describe what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

Unless otherwise stated, percentages and ratios relating to solvent mixtures are expressed in volume, purity data determined by gas chromatography are expressed in area %, and the remaining percentages and ratios are expressed in weight. Temperatures are in degrees celsius (°C.), normal pressure is about 1 atmosphere, and room temperature is about 23° C.

EXAMPLE 1 a) 1.74 g of 2,3-difluorobenzeneboric acid and 0.15 g of tetrakis-(triphenylphospine)palladium (0) and subsequently 15 ml of 2M sodium carbonate solution are added while stirring to a solution of 3.75 g of 4-pentyl-biphenyl-4'-trifluoromethylsulphonate in 30 ml of dimethoxyethane. The, the mixture is held at reflux temperature for 15 hours, subsequently cooled, partitioned between water and diethyl ether and the organic phase is dried over anhydrous magnesium slulphate. After evaportion of the solvent the residue is chromatographed on silica gel with 3% ethyl acetate in petroleum ether. Yield: 3.15 g of colourless, solid 1-[4-(4-pentylphenyl)-phenyl]-2,3-difluorobenzene.

b) 6.45 ml of 1.6N butyllithium solution in n-hexane are added dropwise within 5 minutes at −50° C. to a solution of 3.15 g of 1-[4-(4-pentylphenyl)-phenyl]-2,3-difluorobenzene and the reaction mixture is left to react at the same temperature for 3 hours. Then, a solution of 652 mg of propionaldehyde in 4 ml of tetrahydrofuran is added and the mixture is left to warm slowly to room temperature. After 15 hours it is treated with 10 ml of 1N hydrochloric acid, partitioned between methylene chloride and water, the organic phase is washed with saturated sodium bicarbonate solution and dried over anhydrous magnesium sulphate. Evaporation of the solvent and chromatography of the residue on silica gel with 5-20% ethyl acetate in petroleum ether gives 3.2 g of 1-[4-(4-pentylphenyl)-phenyl]-2,3-difluoro-4(1-hydroxypropyl)-benzene.

c) A solution of 3.2 g of 1-[4-(4-pentylphenyl)-phenyl]-2,3-difluoro-4(1-hydroxypropyl)-benzene and 0.3 g of p-toluenesulphonic acid in 70 ml of toluene is heated at reflux temperature for one hour, then cooled, washed with saturated sodium bicarbonate solution and dried over anhydrous magnesium sulphate. Evaporation of the solvent gives 1-[4-(4-pentylphenyl)phenyl]-2,3-difluoro-4-(1-propenyl)-benzene as a crude Z/E isomer mixture.

d) A solution of 1.41 g of bromine in 25 ml of chloroform is slowly added dropwise at 0° C. to a solution of 3.03 g of crude 1-[4-(4-pentylphenyl)-phenyl]-2,3-difluoro-4-(1-propenyl)-benzene in 60 ml of chloroform. After 30 minutes 30 ml of 10% sodium bisulphite solution are added, the organic phase is separated, washed several times with water, dried over anhydrous magnesium sulphate and evaporated. 4.3 g of 1-[4-(4-pentylphenyl)-phenyl]-2,3-difluoro-4-(1,2-dibromopropyl)-benzene remain as the residue.

e) 2.5 g of potassium tert.butylate are added to a solution of 4.3 g of crude 1-[4-(4-pentylphenyl)-phenyl]-2,3-difluoro-4-(1,2-dibromopropyl)-benzene in 200 ml of tert.butyl methyl ether and the reaction mixture is heated at reflux temperature for 4.5 hours. Thereafter, it is cooled, treated with 50 ml of water and partitioned between water and diethyl ether. The combined organic phases are dried over anhydrous magnesium sulphate, the solvent is evaporated and the residue is chroma-tograped on silica gel with 5% ethyl acetate in petroleum ether. Filtration over Alox (CAMAG, neutral, activity grade 1) and fractional crystallization from ethyl acetate gives 2.04 g of 1-[4-(4-pentylphenyl)-phenyl]-2,3-difluoro-4-(1-propynyl)-benzene, m.p. ($C$-$S_B$) 135.7° C.; $S_B$-N 173° C.; cl.p. (N-I) about 210° C.

The following compounds I are manufactured in an analogous manner:

1-[4-trans-(4-trans-Propyl-cyclohexyl)-cyclohexyl]-2,3-difluoro-4-(1-propynyl)-benzene, m.p. 99.9° C.; cl.p. (N-I) 240° C.

1-(4-Pentylphenyl)-2,3-difluoro-4-(1-propynyl)-benzene, m.p. 45.5° C.

1-(4-Pentylphenyl)-3-fluoro-4-(1-propynyl)-benzene, cl.p. (S-I) 53.3° C.

1-[4-trans-(4-trans-Propyl-cyclohexyl)-cyclohexyl]-3-fluoro-4-(1-propynyl)-benzene, m.p. (C-N) 101.5° C., cl.p. (N-I) > 240° C.

EXAMPLE 2 a) To a solution of 1-bromo-4-pentyl-benzene in 40 ml of toluene are added firstly 40 ml of 2M sodium carbonate solution as well as 0.71 g of tetrakis-(triphenylphosphine)-palladium (0) and thereafter a solution of 4 g of 2,3-difluoro-benzeneboric acid in 20 ml of ethanol and the reaction mixture is held at reflux temperature. Then, it is cooled, partitioned between water and diethyl ether, the organic phase is dried over anhydrous magnesium sulphate and the organic phase is evaporated. Chromatography on silica gel with petroleum ether gives 3.49 g of 1-(4-pentylphenyl)-2,3-difluoro-benzene.

b) A solution of 4.6 ml of butyllithium (1.6N) in n-hexane is added dropwise within 5 minutes at −70° C. to a solution of 1.75 g of 1-(4-pentylphenyl)-2,3-difluoro-benzene in 15 ml of dry tetrahydrofuran. After 3 hours at −70° C. a solution of 0.838 g of trimethyl borate in 10 ml of dry tetrahydrofuran is added dropwise at the same temperature within 15 minutes, the mixture is then left to warm slowly to room temperature and held at this temperature for 15 hours. Subsequently, 5 ml of 1N hydrochloric acid are added, the mixture is stirred for about 30 minutes and then partitioned between diethyl ether and water. The organic phase is thereupon extracted with 1N sodium hydroxide solution, the aqueous phase is then made acid with concentrated hydrochloric acid, extracted with methylene chloride and dried over anhydrous magnesium sulphate. After filtration and evaporation of the solvent 1.78 g of 4-(4-pentyl-phenyl)-2,3-difluoro-benzeneboric acid remain as an oily mass.

c) A solution of 1 g of 1-(1-propynyl)-4-bromo-benzene (produced from 4-bromobenzaldehyde by Wittig reaction, bromination of the resulting ethane and bromine elimination analogously to Example 1e) is reacted with 700 mg of tetrakis(triphenylphosphine)palladium (0) and 1.53 g of 4-(4-pentylphenyl)-2,3-difluoro-benzeneboric acid as described under a). Chromatography on silica gel with 3% ethyl acetate in petroleum ether and fractional crystallization from ethyl acetate gives 0.84 g of 1-(4-pentylphenyl)-2,3-difluoro-4-[4-(1-propynyl)-phenyl]benzene, m.p. 102.9° C.; cl.p. (N-I) 198.9° C.

EXAMPLE 3 a) A solution of 10.2 ml of trifluoromethanesulphonic acid in 10 ml of methylene chloride is added dropwise at room temperature to a solution of 51 g of 4-(4-bromophenyl)-propiophenone (produced by acylating p-bromobiphenyl) in 150 ml of methylene chloride and 25 ml of 2,6-di-tert-butylpyridine and the mixture is stirred for 15 hours. Then, it is cautiously added dropwise to a saturated sodium bicarbonate solution, the organic phase is separated, washed, dried over anhydrous magnesium sulphate and evaporated. The residue (49.5 g) is digested with petroleum ether, cooled to −20° C. and filtered off under suction. Chromatography of the solid (15.7 g) on silica gel with 10% ethyl acetate in petroleum ether and subsequent filtration over Alox (CAMAG, neutral, activity grade 1) gives 9.76 g of pure 1-(4-bromophenyl)-4-(1-propynyl)-benzene.

b) Reaction of 0.915 g of 1-(4-bromophenyl)-4-(1-propynyl)-benzene with 1 g of 2,3-difluoro-4-pentyl-benzene boric acid analogously to Example 2c gives 0.7 g of 1-{4-[4-(1-propynyl)-phenyl]-phenyl}-2,3-difluoro-4-pentyl-benzene, m.p. 127° C.; cl.p. (N-I) 216° C.

The following compound I is manufactured in an analogous manner:

1-[4-(1-Propynyl)-phenyl]-2,3-difluoro-4-pentyl-benzene, m.p. 52.5° C.

EXAMPLE 4

Several binary mixtures, each from 4-(trans-4-pentyl-cyclohexyl)-benzonitrile (5 CP) and a particular compound of formula I, were prepared in order to investigate the properties of the compounds of formula I in mixtures (M). The influence on the clearing point (cl.p.), on the threshold potential V10 [the voltage in volt (V) for 10% transmission in the viewing direction perpendicular to the surface of the plates], on the response times t in milliseconds (switching-on time $t_{on}$ and, respectively, switching-off time $t_{off}$) as well as on the optical anisotropy Δn were investigated, V10, $t_{on}$ and $t_{off}$ were measured at 22° C. in a TN cell (low bias tilt) having a plate separation of 8 μm; the 2.5-fold value of the threshold potential V10 was chosen as the operating voltage.

The components of formula I used, their concentration in the respective binary mixture and the measured data are compiled in the following Table. For comparison, the corresponding values for pure 4-(trans-4-pentyl-cyclohexyl)-benzonitrile are also given. Finally, the calculated α-values are also tabulated, whereby $$\alpha = \frac{cl.p.(5CP) \cdot t_{off}(M)}{cl.p.(M) \cdot t_{off}(5CP)}.$$

TABLE

Binary mixtures with 4-(trans-4-pentyl-cyclohexyl)-benzonitrile

| Component of formula I, concentration in the BM in wt. % | Cl.p. (°C.) | V10 (V) | $t_{on}$ (ms) at 22° C. | $t_{off}$ (ms) at 22° C. | Δn | α |
|---|---|---|---|---|---|---|
| [100% 4-(trans-4-Pentyl-cyclohexyl)-benzonitrile] | 54.6 | 1.64 | 22 | 40 | 0.120 | 1.00 |
| 1-(4-Pentylphenyl)-2,3-difluoro-4-(1-propynyl)-benzene, 10% | 49.0 | 1.56 | 26 | 44 | 0.129 | 1.23 |
| 1-(4-Pentylphenyl)-2,3-difluoro-4-(1-propynyl)-benzene, 20% | 44.1 | 1.39 | 31 | 55 | 0.135 | 1.70 |
| 1-(4-Pentylphenyl)-2,3-difluoro-4-[4-(1-propynyl)-phenyl]-benzene, 10% | 62.6 | 1.74 | 27 | 46 | 0.132 | 1.00 |
| 1-(4-Pentylphenyl)-2,3-difluoro-4-[4-(1-propynyl)-phenyl]-benzene, 20% | 72.6 | 1.90 | 29 | 48 | 0.162 | 0.90 |
| 1-{4-[4-(1-Propynyl)-phenyl]-phenyl}-2,3-difluoro-4-pentyl-benzene, 10% | 60.1 | 1.66 | 27 | 43 | 0.137 | 0.98 |
| 1-{4-[4-(1-Propynyl)-phenyl]-phenyl}-2,3-difluoro-4-pentyl-benzene, 20% | 74.1 | 1.86 | 30 | 48 | 0.163 | 0.88 |
| 1-[4-(1-Propynyl)-phenyl]-2,3-difluoro-4-pentyl-benzene, 10% | 49.6 | 1.62 | 27 | 44 | 0.129 | 1.21 |
| 1-[4-(1-Propynyl)-phenyl]-2,3-difluoro-4-pentyl-benzene, 20% | 44.6 | 1.55 | 29 | 49 | 0.135 | 1.50 |

We claim:
1. A compound of the formula

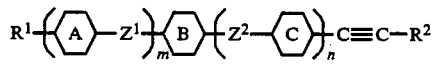

wherein
rings A and C each individually are trans-1,4-cyclohexylene, 1,4-phenylene, trans-1,3-dioxane-2,5-diyl, pyridine-2,5-diyl or pyrimidine-2,5-diyl, provided that not more than one of rings A and C is pyridine-2,5-diyl or pyrimidine-2,5-diyl, wherein the position of the nitrogen atom in the pyridine-2,5-diyl ring and pyrimidine-2,5-diyl, respectively, is directed only in the direction of the triple bond —C≡C—, ring B is 2,3-difluoro-substituted 1,4-phenylene, $Z^1$ or $Z^2$ is a single covalent bond and $Z^2$ or $Z^1$, respectively, is a single covalent bond, ethylene, oxymethylene or methyleneoxy, m and n are each a number 0 to 2, and the sum m+n is 1 or 2, $R^1$ is $C_{1-10}$-alkyl, $C_{2-9}$-alkoxyalkyl or $C_{1-9}$-alkoxy and $R^2$ is $C_{1-10}$-alkyl, with the proviso that two 1,4-phenylene rings are linked with each other only by a single covalent bond.

2. A compound of claim 1, wherein ring A is trans-1,4-cyclohexylene or 1,4-phenylene.

3. A compound of claim 1, wherein ring B is 2,3-difluoro-1,4-phenylene.

4. A compound of claim 2, wherein ring B is 2,3-difluoro-1,4-phenylene.

5. A compound of claim 1, wherein ring C is trans-1,4-cyclohexylene or 1,4-phenylene.

6. A compound of claim 2, wherein ring C is trans-1,4-cyclohexylene or 1,4-phenylene.

7. A compound of claim 3, wherein ring C is trans-1,4-cyclohexylene or 1,4-phenylene.

8. A compound of claim 1, wherein $Z^1$ signifies a single covalent bond or ethylene.

9. A compound of claim 1, wherein $Z^2$ signifies a single covalent bond or ethylene.

10. A compound of claim 1, wherein $R^1$ contains 3 to 5 carbon atoms.

11. A compound of claim 1, wherein $R^2$ signifies $C_{1-3}$-alkyl.

12. A liquid crystalline mixture having at least two components, wherein at least one component is compound of the formula

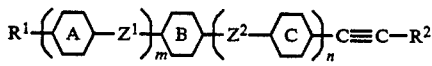

wherein
rings A and C each individually are trans-1,4-cyclohexylene, 1,4-phenylene, trans-1,3-dioxane-2,5-diyl, pyridine-2,5-diyl or pyrimidine-2,5-diyl, provided that not more than one of rings A and C is pyridine-2,5-diyl or pyrimidine-2,5-diyl, with the proviso that the position of the nitrogen atom in the pyridine-2,5-diyl ring and pyrimidine-2,5-diyl, respectively, is directed only in the direction of the triple bond —C≡C—,
ring B is 2,3-difluoro-substituted 1,4-phenylene,
$Z^1$ or $Z^2$ is a single covalent bond and $Z^2$ or $Z^1$, respectively, is a single covalent bond, ethylene, oxymethyleneoxy or methyleneoxy, m and n are each a number 0 to 2, and the sum m+n is 1 or 2,
$R^1$ is $C_{1-10}$-alkyl, $C_{2-9}$-alkoxyalkyl or $C_{1-9}$-alkoxy and $R^2$ is $C_{1-10}$-alkyl,
with the proviso that two 1,4-phenylene rings are linked with each other only by a single covalent bond.

13. A liquid crystalline mixture of claim 12, wherein the concentration of compounds having said formula is within the range of 3 to 30 wt. %.

14. A liquid crystalline mixture of claim 12, which contains at least one compound of said formula and at least one compound selected from the group consisting of compounds of the general formulae

II

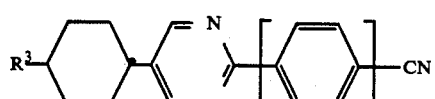
III

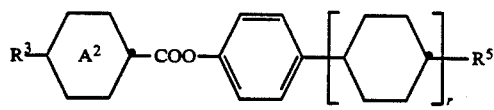
IV

-continued

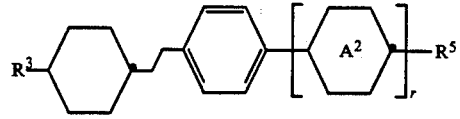
V

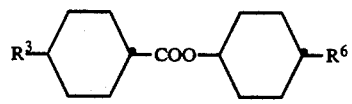
VI

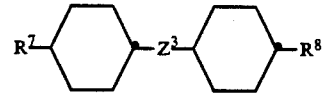
VII

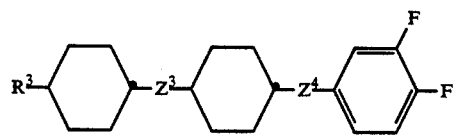
VIII

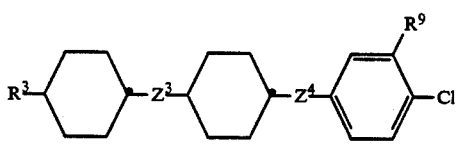
IX

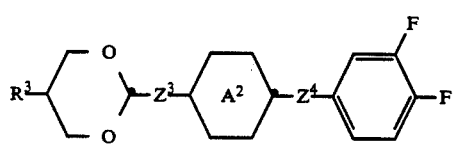
X

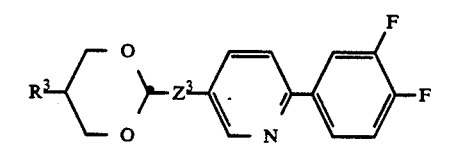
XI

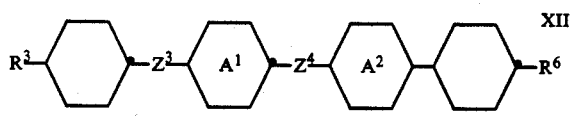
XII

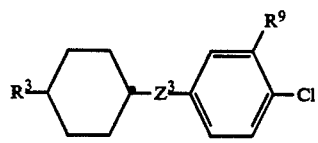
XIII

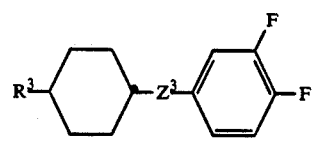
XIV

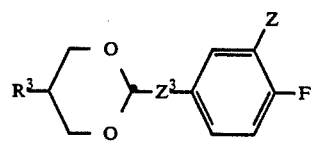
XV

-continued

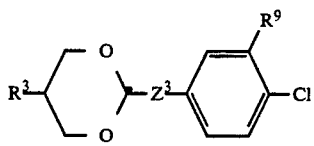

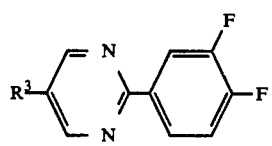

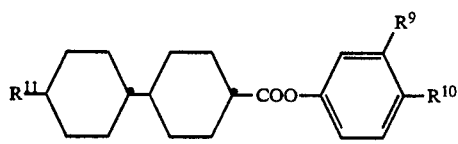

-continued

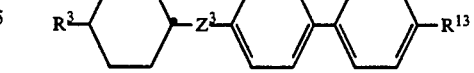

wherein r stands for the number 0 or 1; $R^3$ and $R^6$ are each independently alkyl, alkoxyalkyl, 3E-alkenyl, 4-alkenyl or in the case of a saturated ring also 1E-alkenyl; ring $A^1$ is 1,4-phenylene, trans-1,4-cyclohexylene, pyridine-2,5-diyl, pyrimidine-2,5-diyl or trans-1,3-dioxane-2,5-diyl; $R^4$ is cyano, isothiocyanato, fluorine, alkyl, 3E-alkenyl, 4-alkenyl, alkoxy, 2E-alkenyl-oxy, 3-alkenyloxy, difluoromethoxy, trifluoromethoxy or 1-alkynyl; ring $A^2$ is 1,4-phenylene or trans-1,4-cyclohexylene; $R^5$ is alkyl, 3E-alkenyl, 4-alkenyl or in the case of a cyclohexane ring also 1E-alkenyl or in the case of a benzene ring also cyano, isothiocyanato, alkoxy, 2E-alkenyloxy or 3-alkenyloxy; $R^7$ is alkyl, 1E-alkenyl, 3E-alkenyl or 4-alkenyl; $Z^3$ and $Z^4$ each represent a single covalent bond or ethylene, whereby two aromatic rings are linked, only by a single covalent bond; $R^8$ is cyano, alkyl, 1E-alkenyl, 3E-alkenyl, 4-alkenyl, alkoxy, 2E-alkenyloxy, 3-alkenyloxy, alkoxymethyl or (2E-alkenyl)oxymethyl; $R^9$ is hydrogen, fluorine or chlorine; $R^{10}$ is fluorine, chlorine, difluoromethoxy, trifluoromethoxy or cyano; $R^{11}$ is alkyl, 1E-alkenyl, 3E-alkenyl or 4-alkenyl; $R^{12}$ is hydrogen or fluorine; and $R^{13}$ is fluorine, chlorine, difluoromethoxy or trifluoromethoxy.

* * * * *